(12) United States Patent
Lyon

(10) Patent No.: US 9,078,693 B2
(45) Date of Patent: *Jul. 14, 2015

(54) METHOD AND APPARATUS FOR ASPIRATION

(76) Inventor: Thomas R. Lyon, Brooklyn, NY (US)

( * ) Notice: Subject to any disclaimer, the term of this patent is extended or adjusted under 35 U.S.C. 154(b) by 173 days.

This patent is subject to a terminal disclaimer.

(21) Appl. No.: 13/352,280

(22) Filed: Jan. 17, 2012

(65) Prior Publication Data

US 2012/0203197 A1   Aug. 9, 2012

Related U.S. Application Data

(63) Continuation of application No. 12/676,396, filed as application No. PCT/US2007/019267 on Sep. 4, 2007, now Pat. No. 8,123,699.

(51) Int. Cl.
*A61B 10/00* (2006.01)
*A61B 17/34* (2006.01)
*A61B 10/02* (2006.01)

(52) U.S. Cl.
CPC ..... *A61B 17/3403* (2013.01); *A61B 2010/0258* (2013.01); *A61B 2017/3407* (2013.01); *A61B 2017/3411* (2013.01)

(58) Field of Classification Search
CPC .................. A61B 17/3403; A61B 2017/3707; A61B 2017/3411; A61B 2010/0258
USPC ...................... 604/272, 264, 275; 606/80, 93; 600/564–567
See application file for complete search history.

(56) References Cited

U.S. PATENT DOCUMENTS

| | | | |
|---|---|---|---|
| 2,531,734 | A | 11/1950 | Hopkins |
| 4,808,157 | A | 2/1989 | Coombs |
| 5,012,818 | A | 5/1991 | Joishy |
| 5,372,583 | A | 12/1994 | Roberts et al. |
| 5,660,186 | A | 8/1997 | Bachir |
| 5,954,671 | A | 9/1999 | O'Neill |
| 6,210,376 | B1 | 4/2001 | Grayson |
| D489,456 | S | 5/2004 | Groenke et al. |
| 6,890,308 | B2 | 5/2005 | Islam |
| 6,916,292 | B2 | 7/2005 | Morawski et al. |

(Continued)

FOREIGN PATENT DOCUMENTS

| | | |
|---|---|---|
| CN | 1058142 | 1/1992 |
| EP | 0513446 | 2/1991 |

(Continued)

OTHER PUBLICATIONS

A New Single-Use Bone Marrow Biopsy Needle by Islam, A. Dept of Medicine, Buffalo Gen. Hosp., N.Y., Sep. 2005.

*Primary Examiner* — Laura Bouchelle
(74) *Attorney, Agent, or Firm* — Harold G. Furlow, Esq

(57) ABSTRACT

An aspiration apparatus is described that includes a guide and a set of needles. The guide preferably has an approximately conical shape with a decreasing diameter in the distal direction. A plurality of lumens extend between a distal end portion and a proximal end portion of the guide. The needles have a tubular wall and are slidingly positionable in the lumens. The needles include a longitudinal section of the tubular wall that has a plurality of apertures that decrease in size in the proximal direction. The apertures define an approximately conically shaped area of harvest. The aspiration apparatus can connect to an external source of reduced pressure through the guide or directly to each needle.

19 Claims, 12 Drawing Sheets

(56) References Cited

U.S. PATENT DOCUMENTS

| | | |
|---|---|---|
| 7,175,336 B2 | 2/2007 | Voellmicke et al. |
| 8,123,699 B2 * | 2/2012 | Lyon ............................. 600/567 |
| 2003/0009132 A1 * | 1/2003 | Schwartz et al. ............. 604/152 |
| 2003/0050574 A1 | 3/2003 | Krueger |
| 2003/0055373 A1 | 3/2003 | Sramek et al. |
| 2003/0139688 A1 | 7/2003 | Lamoureux et al. |
| 2003/0233114 A1 | 12/2003 | Merboth et al. |
| 2004/0077973 A1 | 4/2004 | Groenke et al. |
| 2004/0097828 A1 | 5/2004 | Pellegrino et al. |
| 2004/0153005 A1 | 8/2004 | Krueger |
| 2004/0191897 A1 | 9/2004 | Muschler |
| 2004/0267154 A1 | 12/2004 | Sutton et al. |
| 2005/0021067 A1 | 1/2005 | Kim |
| 2005/0209564 A1 | 9/2005 | Bonner et al. |
| 2006/0167379 A1 | 7/2006 | Miller |
| 2006/0189996 A1 | 8/2006 | Orbay et al. |
| 2007/0016100 A1 | 1/2007 | Miller |
| 2007/0055291 A1 | 3/2007 | Birkmeyer et al. |
| 2009/0149774 A1 | 6/2009 | Simon et al. |

FOREIGN PATENT DOCUMENTS

| | | |
|---|---|---|
| FR | WO2005/041790 A2 | 10/2004 |
| GB | 2130890 | 11/1983 |
| JP | 2004344299 A | 5/2003 |
| JP | 2005087519 A | 9/2003 |
| JP | 2005087520 A | 9/2003 |
| JP | 2004136106 | 12/2003 |
| JP | 2005087521 A | 4/2005 |

* cited by examiner

FIG. 7
FIG. 8
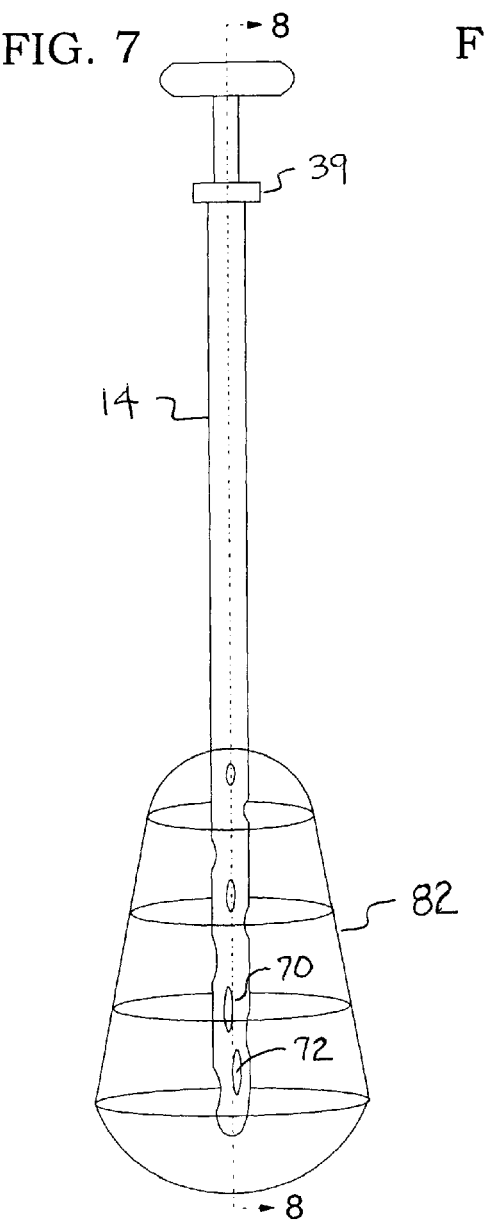
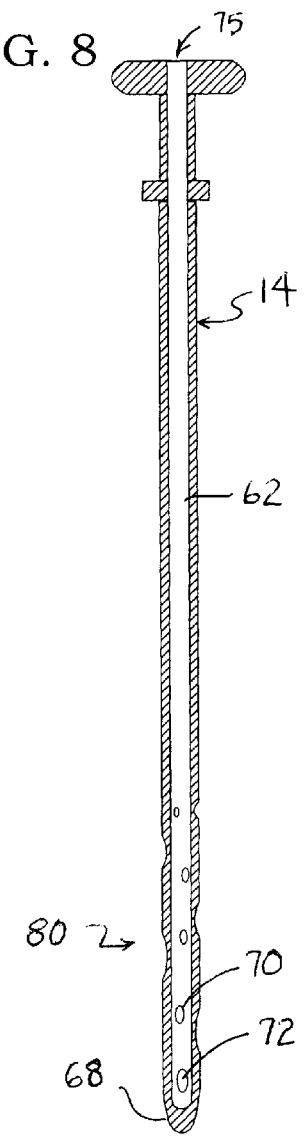

METHOD AND APPARATUS FOR ASPIRATION

CROSS-REFERENCE TO RELATED APPLICATIONS

This is a continuation of U.S. patent application Ser. No. 12/676,396 filed on Mar. 4, 2010, initially filed as PCT/US2007019267 filed on Sep. 4, 2007.

FIELD OF THE INVENTION

The present invention relates to aspiration apparatuses and more specifically to an aspiration apparatus that includes a guide that directs one or more needles for aspiration.

BACKGROUND OF THE INVENTION

Bone marrow is often used in orthodpaedic procedures to augment fracture healing. It is also an excellent source of mesenchymal stem cells (MSC's) and/or tissue progenitor cells (TPC's). These multi-potent cells have broad applications in addition to orthopaedics and may be used in the fields of cardiology, oncology and other areas. As new techniques are being developed to use these cells and to culture them ex-vivo it has become increasingly important to be able to procure large volumes of highly cellular marrow from the body.

At present, the pelvis is the source for almost all of the marrow that is used for mesenchymal stem cells. Obtaining marrow from the pelvis, however, can be difficult and may present risks to the abdominal cavity, especially when obesity obscures normal landmarks. Additionally, patients undergoing lower extremity procedures such as ankle or tibia fractures often do not have the pelvis readily accessible for sterile bone marrow access.

A further problem is that the aspiration of more than approximately two to four cubic centimeters of marrow in one area has been shown to result in the subsequent withdrawal of local "venous blood" as opposed to marrow and therefore significantly deceases the MSC/TPC count. This requires the frequent removal and redirection of the needle and can further include the creation of one or more additional points of access into the bone in order to avoid overlapping areas that have already been "tapped out" of marrow. Further, each additional point of access into the bone creates additional risks to the abdominal cavity.

An apparatus is needed for the harvesting of marrow from a bone that can be fixed relative to a bony landmark and guide multiple needles through that single penetration in the bone to harvest an increased volume of marrow.

SUMMARY OF THE INVENTION

A guide for the directional orientation of aspirating needles is described that comprises a body that has a distal end portion and a proximal end portion. The distal end portion and proximal end portion define a central longitudinal axis. A plurality of lumens is defined in the body and each lumen has a distal opening in the distal end portion and a proximal opening in the proximal end portion. Each lumen of the plurality of lumens defines an axis that has a acute oblique angle relative to the central longitudinal axis such that the axes of the lumens diverge from the central longitudinal axis as the axes of the lumens exit from the distal opening. A fastener is positioned proximal to the distal end portion on the body. The fastener is adapted to fix the body in the bone of a patient for the harvesting of tissue through the distal openings of the lumens in the distal end portion of the body.

The body can include an interior chamber that is in fluid communication with the plurality of lumens. The body can also include a guide needle that extends distally from the distal end portion of the body. The guide needle is in fluid communication with the chamber. The body defines a lumen that extends between the chamber and a port in the proximal end portion. The port includes a fluid tight connector.

The guide can further include a set of needles. The needles have distal end portions and proximal end portions. Each needle has a tubular wall that defines a lumen. A longitudinal section of the tubular wall includes a plurality of apertures that are in fluid communication with the lumen. The size of the apertures in the tubular wall varies to define a desired shape of an area of harvest surrounding the longitudinal section.

The proximal openings of the lumens in the body include a seat and the proximal portion of the needles has a key. The needles have a first position wherein the needles are separate from the guide and a second position wherein the key of the needle is connected to the seat and the longitudinal section of the needle is positioned distal to the distal opening of the lumen in the body. The tubular wall of each needle defines a lumen that has a proximal terminal end aperture in the tubular wall and when the needle is in the second position the proximal terminal end aperture is in fluid communication with the chamber.

The guide is adapted to couple with a source of reduced pressure. The source of reduced pressure can be coupled to the fluid tight connector of the port in the proximal end portion. The source of reduced pressure draws fluid through the apertures of the needles, the lumens of the needles, into the chamber and through the proximal port of the body.

The proximal end portion of the needles includes a proximal opening of the lumen and the proximal opening includes a fluid tight connector. The external source of reduced pressure can be connected to the proximal opening of each needle.

A needle for use in aspiration is described that comprises an elongate tubular needle that includes a distal end portion and a proximal end portion that define a longitudinal axis. The needle has a tubular sidewall and the distal end portion includes a distal tip. A longitudinally aligned lumen is defined by the sidewall that has a distal terminal end in proximity to the distal tip and an opposed proximal aperture. The proximal aperture is adapted to be coupled with a source of reduced pressure.

A region of the sidewall extends between a distal end in proximity to the distal tip and a proximal end proximal to the proximal aperture. The region includes a plurality of apertures and each aperture of the plurality of apertures defines an area in the sidewall that is in fluid communication with the lumen. The area of each aperture in the region decreases in proximal direction.

An approximately conically shaped harvest area is defined by the plurality of apertures in the region when the source of reduced pressure is applied to the lumen, the conically shaped harvest area having a first distal volume that tapers to a reduced second proximal volume in proximity to a proximal end of the region. The lumen has a proximal terminal end that is in proximity to the proximal aperture and the proximal aperture is an aperture in the sidewall. The needle proximal end portion defines the proximal aperture.

A method of aspirating using an aspiration apparatus is described comprising the steps of providing an aspiration apparatus including a guide and a set of needles. The guide includes a distal end portion and a proximal end portion that define a central longitudinal axis. A plurality of lumens defines a plurality of distal openings in the distal end portion of the body and a plurality of proximal openings in the proximal end portion of the body. The lumens having an acute oblique angle relative to the central longitudinal axis such that the alignment of the lumens diverges as it extends from the distal openings in the guide. The guide includes a fastener positioned proximal to the distal end portion that is adapted to fix the guide in the bone relative to the patient and provide access through the one incision for the distal end portion of guide that includes a plurality of distal lumen openings.

The method includes making an incision into the tissue and bone of a patient, positioning a guide of the aspiration apparatus at least partially into the incision and fixing the guide in position in the incision with the distal end portion of the guide inside the bone of the patient. Positioning a set of needles in a first position relative to the guide. The needles in the second position have a longitudinal section that extends from the distal opening of the lumen in the distal end portion of the guide to the distal end portion of the needle.

An external source of reduced pressure can be connected to the aspiration apparatus to draw marrow through the needles. The longitudinal section of the needles has an arrangement of apertures that decreases the spacing between the apertures in the distal direction. The guide needle is approximately aligned with the longitudinal axis. The aspirated fluid is collected in a chamber in the guide. The aspirated fluid is drawn from the chamber through the body using the external source of reduced pressure that is connected to the port of the guide. The collecting of the aspirated fluid or tissue can also be done directly from the proximal end portion of each needle by an external source of reduced pressure.

BRIEF DESCRIPTION OF THE DRAWINGS

Preferred embodiments of the invention are described below with reference to the drawings, wherein like numerals are used to refer to the same or similar elements.

FIG. 7 is a side view of the one needle of the set of needles of FIG. 5;

FIG. 8 is a cross-sectional view taken along lines 8-8 of the needle of FIG. 7;

DETAILED DESCRIPTION

Figure 1:
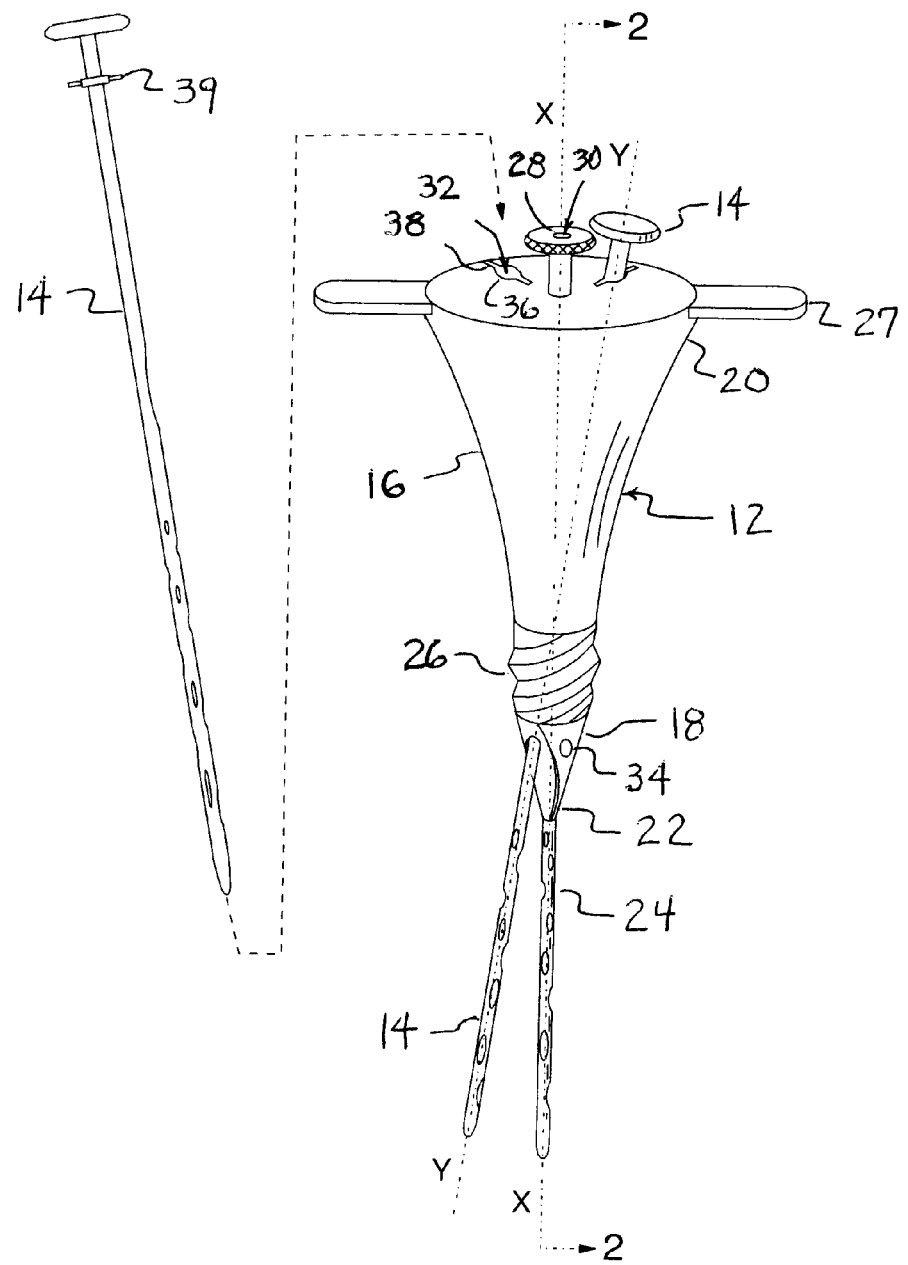
FIG. 1 is a front and top perspective view of an aspiration apparatus constructed in accordance with the present disclosure that includes a guide, one needle of a set of needles is in a first position separate from the guide and one needle is in a second position seated in the guide.

Referring initially to FIG. 1, an aspiration apparatus 10 includes a guide 12 that provides directional alignment for one or more needles 14 of a set of needles. Guide 12 has a body 16 with a distal end portion 18 and a proximal end portion 20. Body 16 preferably has an approximately conical shape. In this preferred embodiment, body 16 has a distal end portion 18 has a first diameter that is less than a second diameter of proximal end portion 20. Distal end portion 18 and proximal end portion 20 define a central longitudinal axis-X. Aspiration apparatus 10 can selectively further include the set of needles. In this preferred embodiment, the set of needles has two needles 14. As shown, aspiration apparatus 10 has one needle 14 in a first position that is unconnected with the set of needles and one needle 14 in a second position seated in guide 12 for operational use.

Distal end portion 18 has a terminal end 22 that connects to a guide needle 24. Guide or guide needle 24 extends distally along the central longitudinal axis-X. Guide 12 includes a fastener 26 that is in proximity to and proximal of distal end portion 18. A cutting edge is preferably defined on at least a portion of the outer side wall of distal end portion 18. Guide 12 can also includes one or more handles 27 that are connected to body 16.

Proximal end portion 20 includes a port 28 for a first lumen 30. Port 28 has a fluid tight connector such as a leer lock that can interface with standard connectors of external medical devices. First lumen 30 is preferably aligned with the central longitudinal axis-X. In this preferred embodiment, guide 12 also includes two lumens 32 that extend between a distal port 34 in distal end portion 18 and a proximal port 36 in proximal end portion 20. In this preferred embodiment, the two distal ports 34 are arranged along radii of central longitudinal axis-X that are approximately ninety degrees apart. Similarly, proximal ports 36 are arranged along radii of central longitudinal axis-X that are approximately ninety degrees apart. It is understood that the number and angular orientation of lumens 32 can vary depending upon the desired application of aspiration apparatus 10.

Each lumen 32 slidingly receives a needle 14 from the set of needles 14. Proximal port 36 limits the longitudinal travel and fixes each needle 14 in guide 12 in a second position of aspiration apparatus 10. In this preferred embodiment the seat limits the distal longitudinal travel and controls the alignment of needles 14. In this preferred embodiment, the alignment of needles 14 includes an alignment device such as a slot 38 that receives a key 39 of needles 14 and fixes the longitudinal travel and radial alignment of needles 14 in a predetermined direction. A fluid tight seal, such as a bias member, is provided between each lumen 32 and needle 14.

Fastener 26 fixes the position and angular orientation of guide 12. Fastener 26 in this preferred embodiment is helical threads that engage the patient's bone to fix the position and angle of guide 12 and is fabricated of one or more of metals, polymers or composite materials that have sufficient hardness to securely engage outer cortical bone. Fastener 26 can include alternative mechanical devices to fix the position of guide 12 relative to the patient such as longitudinally aligned grooves and/or a bias member.

Figure 2:
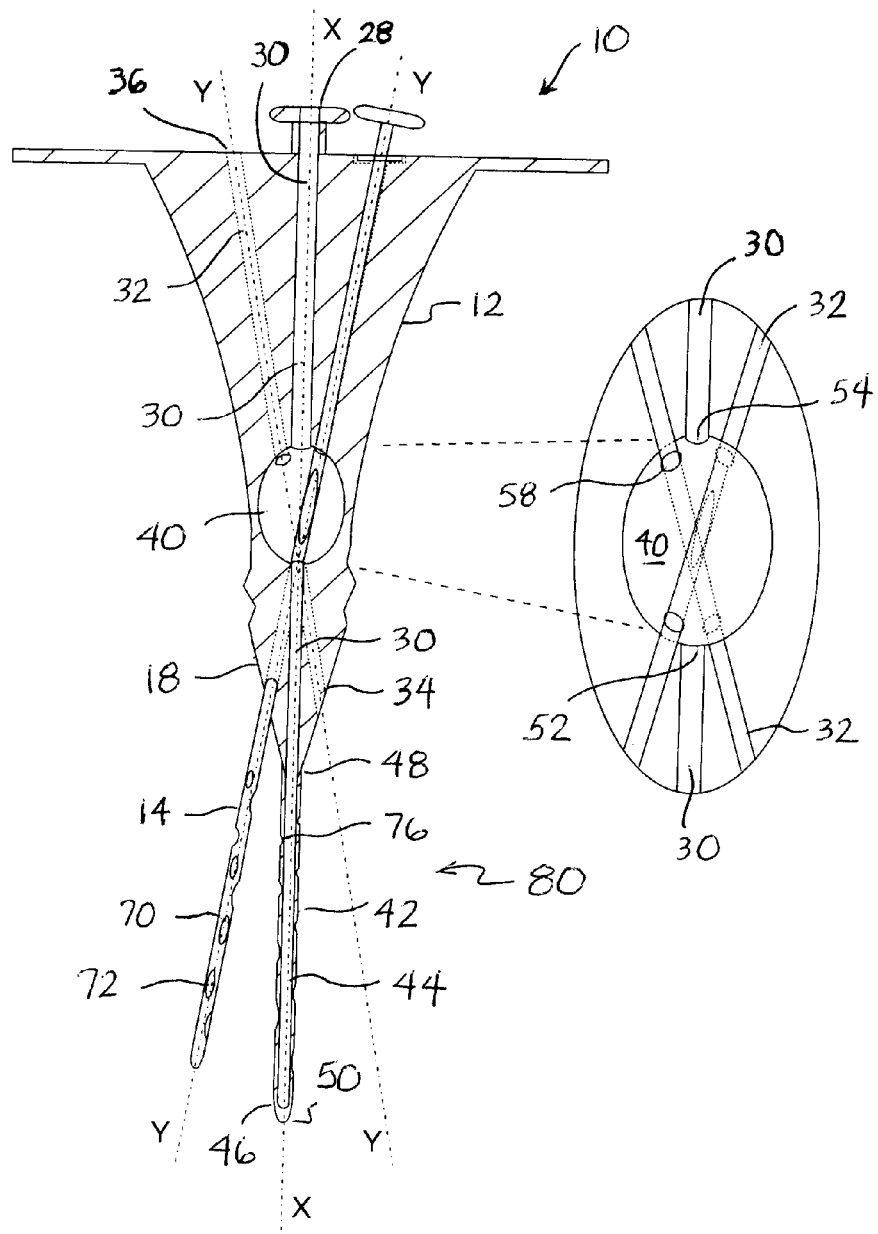
FIG. 2 is a cross-sectional view of the guide of FIG. 1 taken along lines 2-2 showing one needle of the set of needles in the second position.

As shown in FIG. 2, guide 12 defines an interior chamber 40 that is in fluid communication with first lumen 30 and second lumens 32. Guide needle 24 has a tubular wall 42 that defines a lumen 44 that is in fluid communication with first lumen 30 of guide 12. Lumen 44 extends between a distal end portion 46 and a proximal end portion 48 of needle 24. Distal end portion 46 of guide needle 24 includes a terminal end 50 that is a solid point that is suitable for penetrating soft tissue. A first portion of lumen 30 extends between proximal end portion 48 of guide needle 24 and a rim 52 in the wall of chamber 40. A second portion of lumen 30 extends between a rim 54 in the wall of chamber 40 and port 28. Proximal end portion 48 of needle 24 is connected to distal end portion 18 of guide 12.

Each lumen 32 is a through hole that is in fluid communication with chamber 40 and extends proximally from distal port 34 chamber 40 to proximal port 36. In this preferred embodiment, the first portion of lumen 32 extends from port 34 to a distal rim 56 in the wall of chamber 40. A proximal rim 58 is defined in the wall of chamber 40 that extends to proximal port 36. Each lumen 32 defines an axis-Y at an oblique acute angle relative to central longitudinal axis-X. Lumens 32 preferably define straight through holes and axes, but lumens 32 can also be arcuate.

In this preferred embodiment, the angular relationship between axes-Y of lumens 32 is such that axes-Y diverge from each other and longitudinal axis-X upon exiting from distal ports 34. It is understood that the angular relationship between axes-Y and the longitudinal axis-X can vary depending upon the particular application of guide 12. In the second position, needle 14 is fully inserted into and engaged with guide 12.

Figure 3:
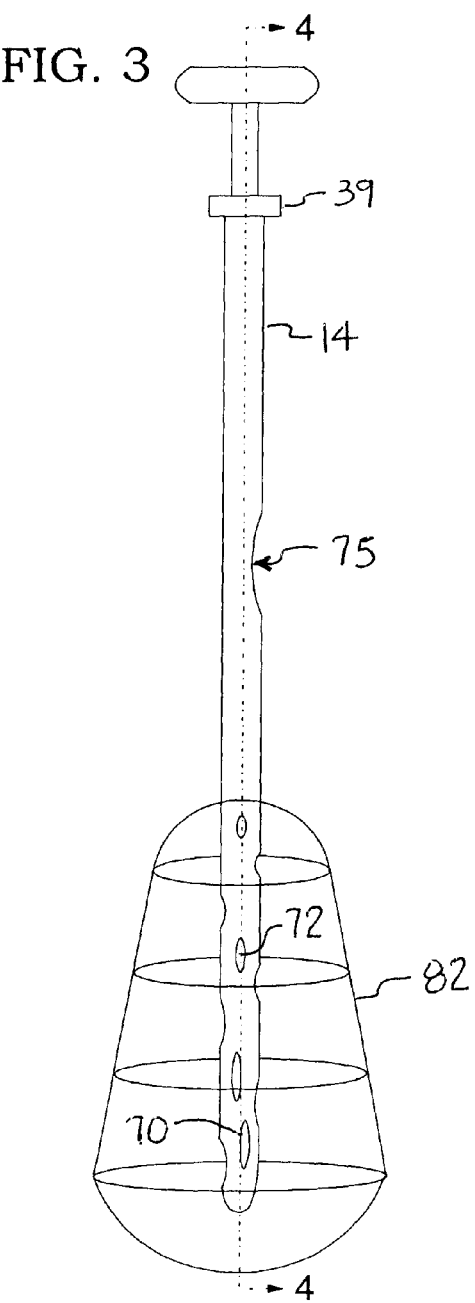
FIG. 3 is a side view of one of the needles of the set of needles of FIG. 1.
Figure 4:
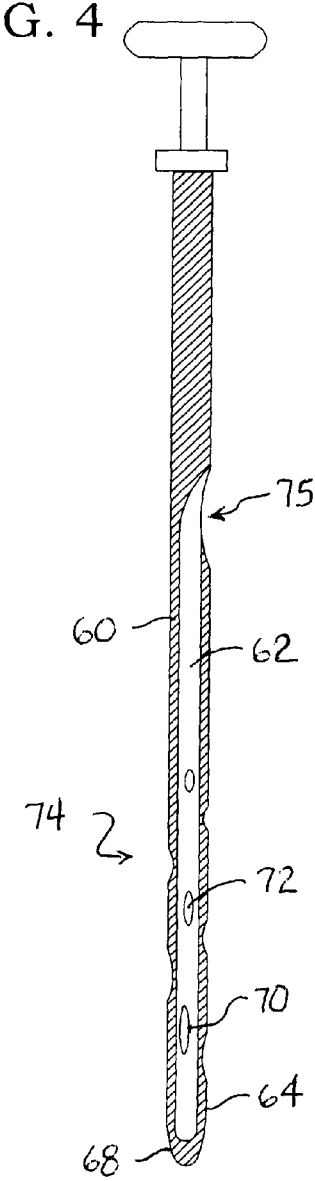
FIG. 4 is a cross-sectional view of the needle of FIG. 3 taken along lines 4-4.

Referring now to FIGS. 2-4, each needle 14 has a distal end portion 64 and a proximal end portion 66. Distal end portion 64 has a distal tip or terminal end 68 that is a solid point that is suitable for penetrating soft tissue. Proximal end portion 66 includes a proximal end. Needle 14 has a tubular wall 60 that defines a lumen 62.

Tubular walls or sidewalls 60 include a plurality of rims 70 that define a plurality of apertures 72. Rims 70 are arranged along a predefined longitudinal section 74 of needles 14 that extends proximally from a region in proximity to distal end portion 64 for a predetermined distance to an area distal to a proximal aperture 75. In this preferred embodiment, longitudinal section 74 extends between distal end portion 64 and a region of needle 14 that extends distally from and is in proximity to distal port 34 of guide 12 when needle 14 is in the second position of aspiration apparatus 10.

Rims 70 formed in a tubular wall 60 define the size or area of apertures 72 through tubular wall 60. The area defined by each rim 70 decreases in the proximal direction from the distal end portion 64 such that the area defined by rims 70 in proximity to the distal end portion 64 are greater than the area defined by rims 70 in proximity to the proximal end of longitudinal section 74. The spacing between, angular orientation of and arrangement of rims 70 in tubular wall 60 can also vary along the length of longitudinal section 74.

Lumen 62 of needle 14 extends from a terminal end in proximity to solid distal tip 68 to a solid wall in proximity to exit or proximal aperture 75. When needle 14 is in the second position in guide 12, slot 38 aligns with key 39 of needle 14 to orient aperture 75 to face into chamber 40. The proximal terminal end or wall of lumen 62 preferably has an arcuate shape that redirects fluid flow through aperture 75 and into chamber 40.

Tubular wall 42 of guide needle 24 defines a plurality of rims 76 that define a plurality of apertures 78. Rims 76 are arranged along a predefined longitudinal section 80 of needles 14. Longitudinal section 80 extends along the longitudinal axis of needle 14 from a region in proximity to distal end portion 46 proximally for a predetermined distance. In this preferred embodiment, longitudinal section 80 extends between distal end portion 46 and a region in proximity to where needle 24 connects to distal end portion 18 of guide 12. Rims 76 define the size or area of apertures 78 through tubular wall 42. The area defined by each rim 76 decreases in the proximal direction from the distal end portion 44 such that the area defined by rims 76 in proximity to the distal end portion 46 are greater than the area defined by rims 76 in proximity to the proximal end of longitudinal section 80. The density of the arrangement of rims 76 in tubular wall 42 can also vary along the length of longitudinal section 80.

As shown in FIG. 3, longitudinal section 74 harvests an approximately conically shaped three-dimensional area or volume of bone marrow harvest 82. The proximal portion of area of harvest 82 is reduced in the proximal regions of longitudinal section 74 by the reduced area or radius and controlled spacing or arrangement of apertures 72 that reduces the fluid flow into lumens 62. This is advantageous because the proximal region longitudinal sections 74 and 80 is where needles 14 and needle 24 are in close proximity and the reduced area and arrangement of apertures 72 and 78 limits the undesirable over harvesting of marrow. Similarly, the distal portion of volume of harvest 82 is increased in the distal regions of longitudinal sections 74 by the larger areas and arrangement of apertures 72 that increases the laminar flow into lumens 62.

The creation of the three dimensional shape of volume of harvest 82 takes into consideration factors such as the arrangement, alignment and the proximally directed decrease in the areas of apertures 72 of needles 14 and apertures 78 of guide needle 24. The desired rate of laminar flow from each of apertures 72 and 78 for a given period of time is preferably systematically calculated using Poiseuille's Law for laminar flow of an incompressible fluid such as high viscosity bone marrow.

Referring again to FIGS. 2-4, the size of area and controlled spacing of apertures 78 in longitudinal section 80 of guide needle 24 is preferably the same as that described above for apertures 72 and longitudinal section 74 of needles 14. The volume of harvest 82 of needle 24 can be increased in the direction away from needles 14 by the increase in size and decrease in spacing between apertures 78. Similarly, the radial alignment provided by slot 38 and key 39 of needle 14 can also include orienting apertures 72 with increased areas in an outward direction and away from the central longitudinal axis-X and/or other needles.

Aspiration apparatus 10 provides a secure fluid tight path of communication from apertures 72 and apertures 78 to port 28. Apertures 72 and apertures 78 are in fluid communication with their respective lumens 62 and lumen 44 of needles 14 and 24, respectively. Lumens 62 terminate at proximal apertures 75 in chamber 40 and lumen 44 is aligned with the first portion of lumen 30 that is in fluid communication with chamber 40. The second portion of lumen 30 provides fluid communication between chamber 40 and port 28. The sealing interface between needles 14 and lumens 32 limits any undesirable intrusion or loss of fluid.

Figure 5:
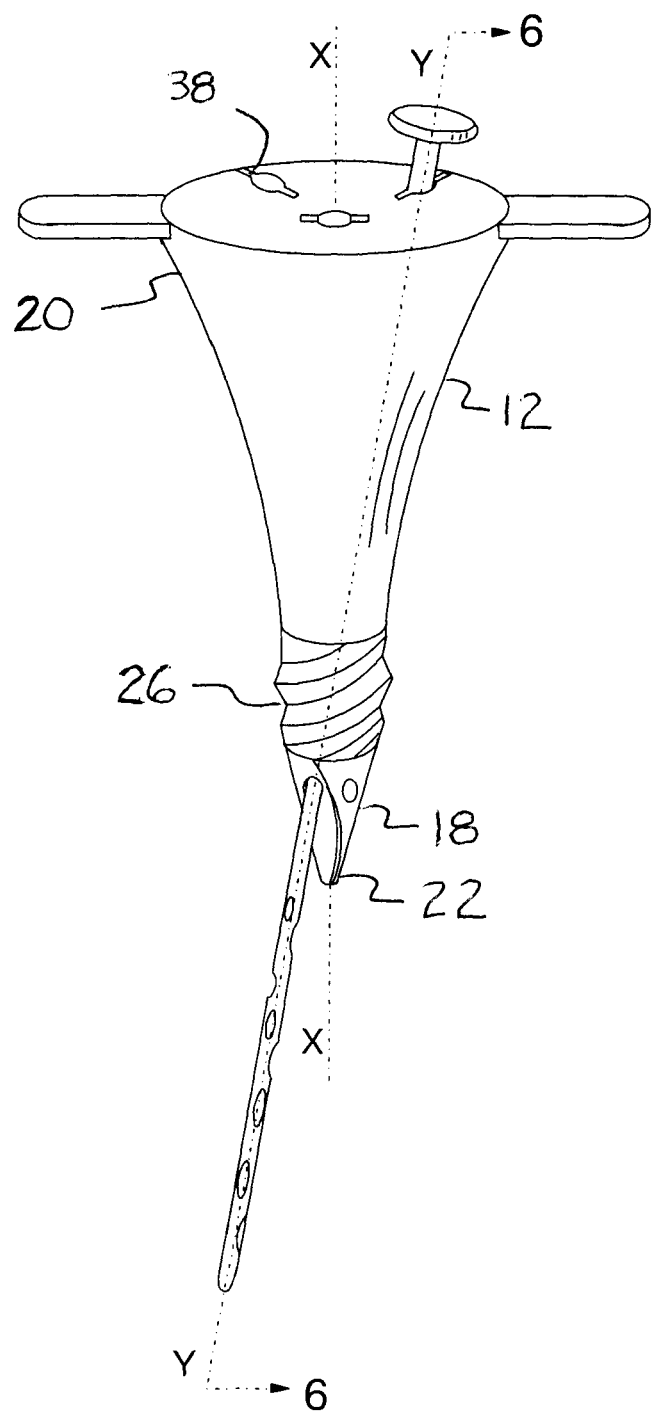
FIG. 5 is a front and top perspective view of a second embodiment of the aspiration apparatus of FIG. 1 constructed in accordance with the present disclosure that includes a guide, one needle of a set of needles is shown in the second position seated in the guide.
Figure 6:
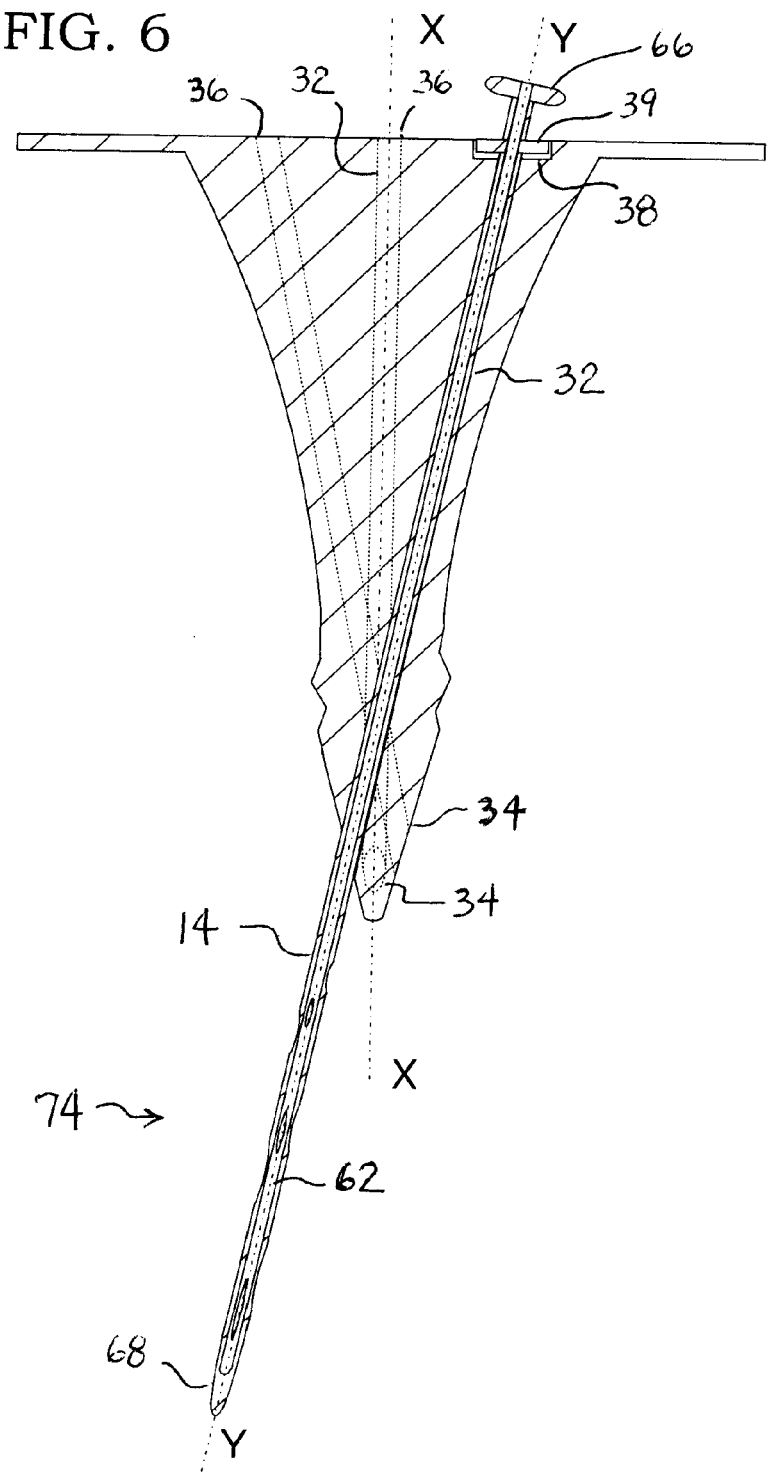
FIG. 6 is a cross-sectional view of the guide of FIG. 5 taken along lines 6-6 with the one needle of the set of needles seated in the second position in the guide.

As shown in FIGS. 5 and 6, a second embodiment of aspiration apparatus 10 includes guide 12 that omits guide needle 24 and has at least one lumen 32. Set of needles 14 can also be included in aspiration apparatus 10. In this preferred embodiment, guide 12 defines three lumens 32. Body 16 has a taper and includes distal end portion 18, proximal end portion 20, terminal end 22, fastener 26, cutting edge and defines a central longitudinal axis-X as described previously in the first embodiment.

Lumens 32 extend between distal ports 34 and proximal ports 36. Distal ports 34 and proximal ports 36 are preferably arranged at approximately 120 degree intervals around central longitudinal axis-X. Each proximal port 36 includes a seat that preferably limits the distal travel and fixes one of needles 14 in the second position. The seat can include a device 38 such as a slot that receives key 39 and fixes the radial position of needle 14 in a single direction. A needle 14 is shown in the second position with a proximal end portion 66 seated in proximal port 36 and longitudinal section 74 extending distally from guide 12.

Referring now to FIGS. 6-8, needle 14 in this preferred embodiment has a lumen 62 that extends between solid distal tip 68 and a proximal aperture 75 defined in proximal end portion 66. In this preferred embodiment of needle 14, aperture 75 is positioned in the proximal end and aligned with longitudinal axis-Y of needle 14. The size of area and controlled spacing of apertures 72 defined by rims 70 control the laminar flow into needle 14 and volume of harvest 82 as described previously. Slots 38 and keys 39 can similarly provide an advantageous directional orientation of increased and/or decreased areas and controlled spacing of apertures 72. In this preferred embodiment of needles 14, apertures 65 of proximal end portions 66 include a fluid tight connector such as a leer lock that can interface with standard connectors of external medical devices.

Aspiration apparatus 10 in the second position with needles 14 seated in guide 12 provides a secure path of fluid communication through lumen 62. Apertures 72 are in fluid communication with each lumen 62 and proximal aperture 75. The sealing interface between needles 14 and lumens 32 limits any undesirable intrusion or loss of fluid.

Guide 12 as well as needles 14 and 24 can be fabricated from any suitable medical grade material to include metals, polymers and composite materials. Guide 12 and needles 14 and 24 can also be fabricated of clear materials or include clear windows positioned at strategic points in guide 12 to enhance the visibility of the aspiration process.

Figure 9:
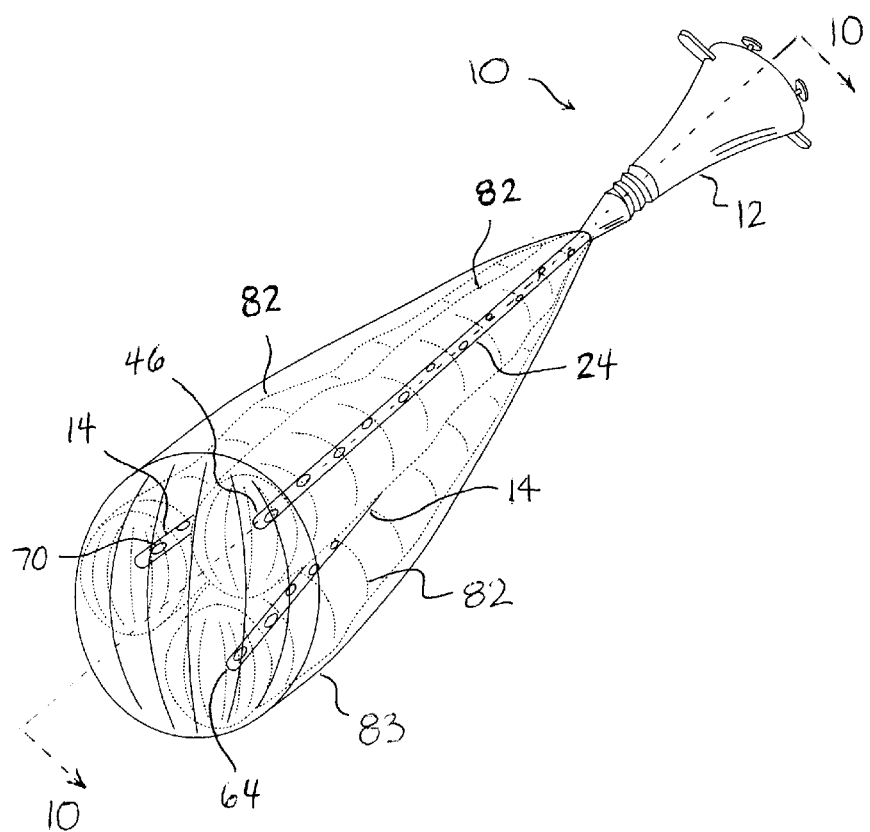
FIG. 9 is a distal perspective view of aspiration apparatus of FIG. 1 with two needles of the set of needles in the second position showing the area of harvest.

As shown in FIG. 9, aspiration apparatus 10 with needles 14 of the set of needles in the second position shows the preferred approximately individual conical shapes 82 of each needle 14 and overall conical shape of the combined harvest volume 83 of the set of needles and guide needle 24. Harvest volume 82 is reduced in proximity to guide 12 and expanded in proximity to distal end portions 64 and 46. Factors such as the size, spacing, angular direction and arrangement of rims 70 and 76 can vary the harvest area 82 of each needle 14 and 24 to minimize the overlap and/or expand the harvest area 82 in select directions. For example, the harvest volume 82 relative to the distal end portions 64 and 46 of needles 14 and 24, respectively, can be relatively flat or approximately hemispherical depending upon the orientation, size and arrangement or rims 70 and 76. Further the combined effect of the volume of harvests 82 can be a greater volume of harvest 83 for aspiration apparatus 10.

Figure 10:
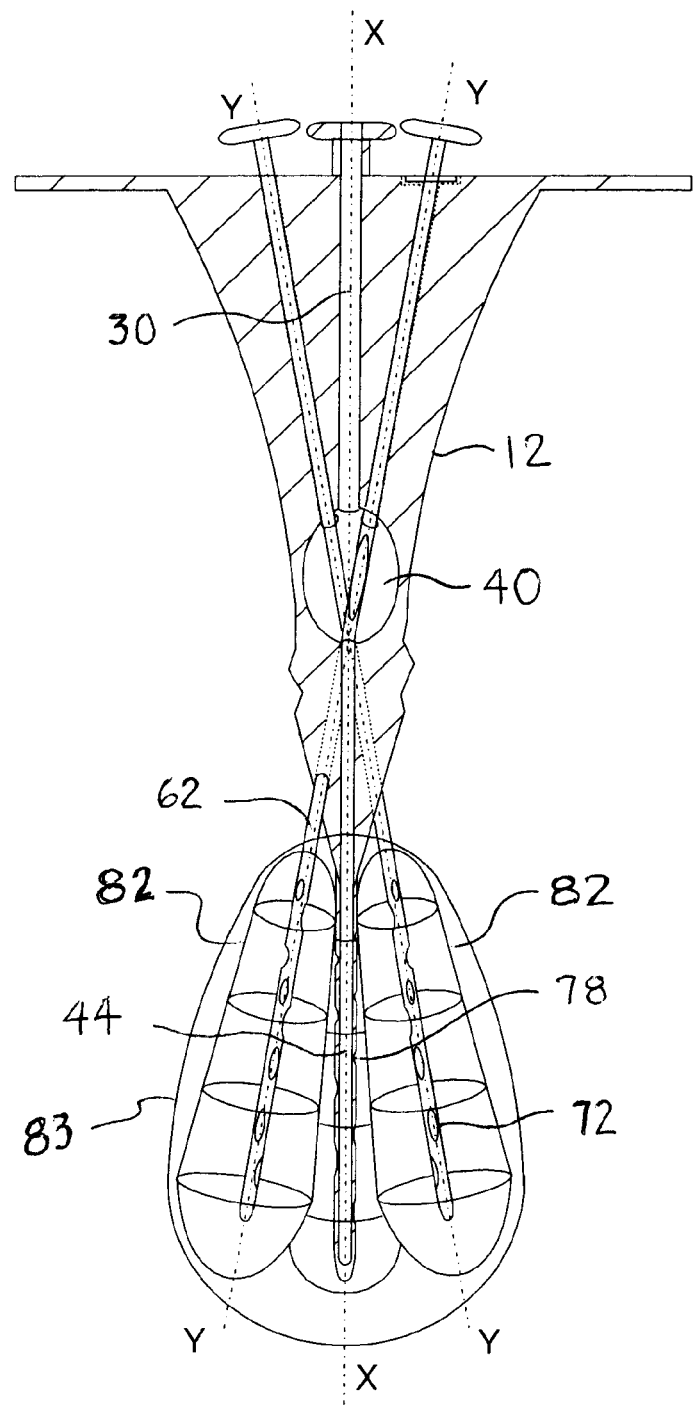
FIG. 10 is a side cross-sectional view taken along lines 10-10 of FIG. 1 with two needles of the set of needles in the second position in the guide.

Referring now to FIG. 10, when port 28 is coupled to a source of reduced pressure, that force applied through apertures 72 and 78 of needles 14 and 24, respectively, produces controlled volumes of harvest 82 and 83. A fluid tight connection is provided through lumens 32 of guide 12, lumens 62 and 44 of needles 14 and 24, respectively, directly into chamber 40 and through first lumen 30.

Figure 11:
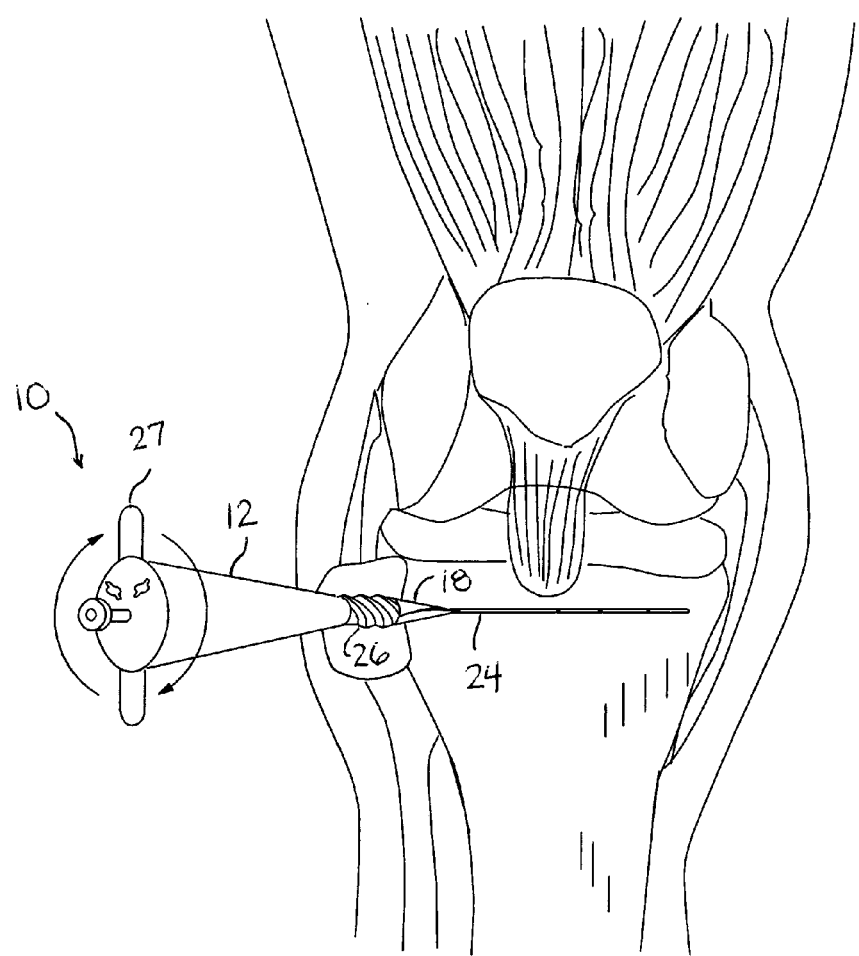
FIG. 11 is a side perspective view of the guide of FIG. 1 being connected to a hard outer cortical bone of a patient.
Figure 12:
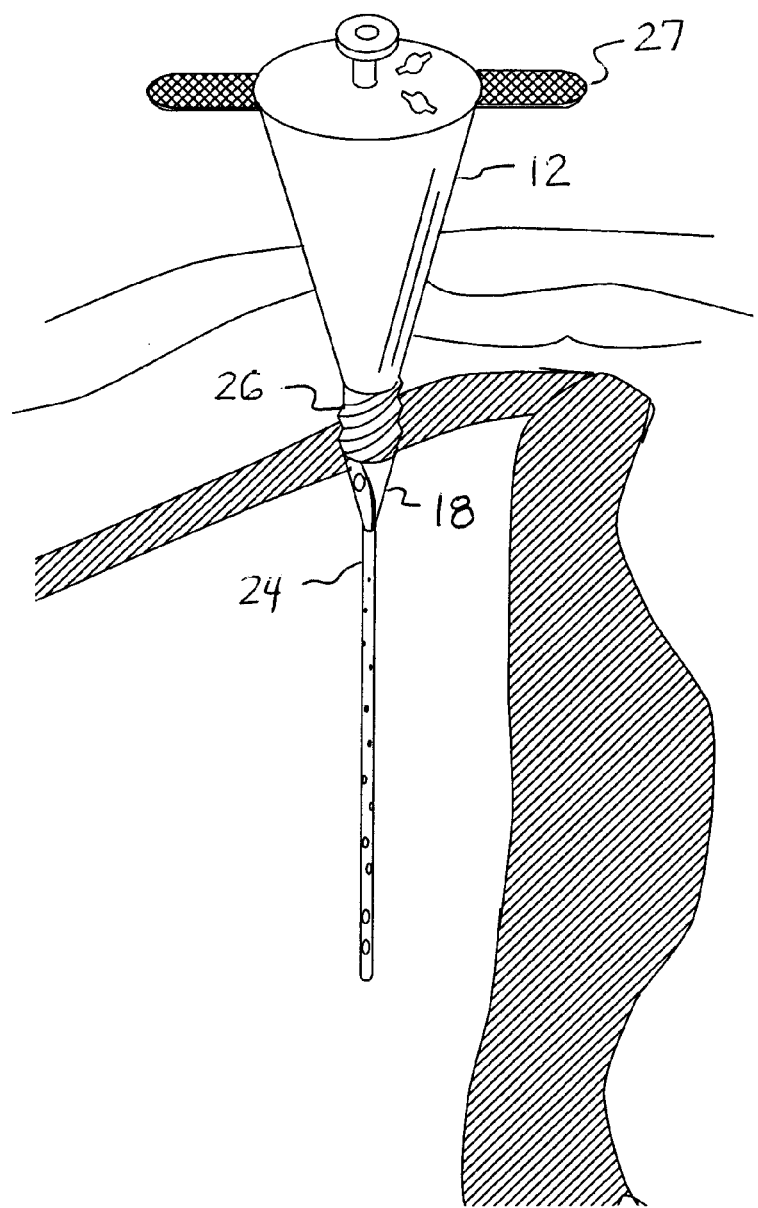
FIG. 12 is a close-up of the side perspective view of the guide of FIG. 11 fixed to the hard outer cortical bone of the patient.

As shown in FIGS. 11 and 12, in operation guide 12 of aspiration apparatus 10 is initially positioned into a small incision made through the skin and outer cortical bone near the proximal tibia. Guide needle 24, when present, and at least a portion of distal end portion 18 of guide 12 is inserted through the incision. Guide 12 is then fastened to the bone of the patient. In this preferred embodiment, guide 12 is rotated about the longitudinal axis so that the cutting edge on the side of distal end portion 18 is used to fasten guide 12 using the initial incision by using handles 27 to rotate guide 12. The continued rotation of guide 12 securely engages fastener 26 with the outer cortical bone. In this preferred embodiment, fastener 26 is a series of helical threads having sufficient hardness to engage outer cortical bone. Fastener 26 enables the user of aspiration apparatus 10 to fix guide 12 in a desired position and at a desired angle of rotation relative to the bone and apertures 34 are position inside the outer cortical bone.

Figure 13:
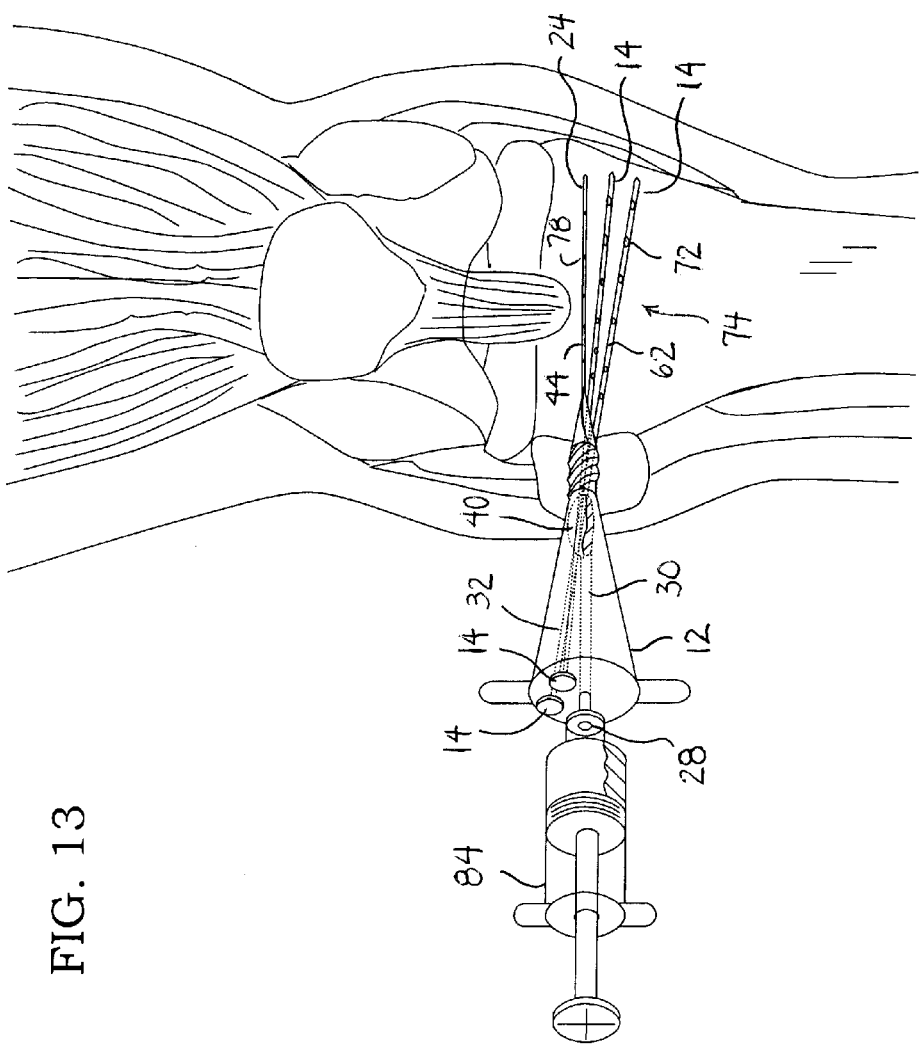
FIG. 13 is the side perspective view of the aspiration apparatus of FIG. 1 showing the set of needles in the second position and a syringe connected to the guide as an external source of reduced pressure for the aspirating of marrow.

Referring now to FIG. 13, guide 12 is fixedly connected to the tibia of the patient and set of needles 14 are placed in the second position in guide 12 such that needles 14 are fully inserted into their respective lumens 32 and longitudinal sections 74 are positioned external to guide 12 and in the marrow. The radial orientation of needles 14 is preferably fixed in this preferred embodiment by inserting keys 39 of needles 14 in slots 38 of proximal end portion 20 of guide 12 (See FIG. 6). Slots 38 provide a limit of travel through guide 12 and a preferred angular orientation for each needle 14.

An external source of reduced pressure 84 such as a syringe with a leur lock interface is secured to proximal port 28. The external source of reduced pressure or syringe 84 in this preferred embodiment generates a reduced pressure through guide 12 and needles 14 in the second position and guide needle 24. This reduced or negative pressure draws marrow through apertures 72 of needles 14 and apertures 78 of needle 24 and into their respective lumens 62 and 44. The marrow is drawn from lumens 62 and 44 into chamber 40. The marrow from apertures 72 and 78 is then drawn through the second portion of lumen 30 and proximal port 28 into syringe 84.

Figure 14:
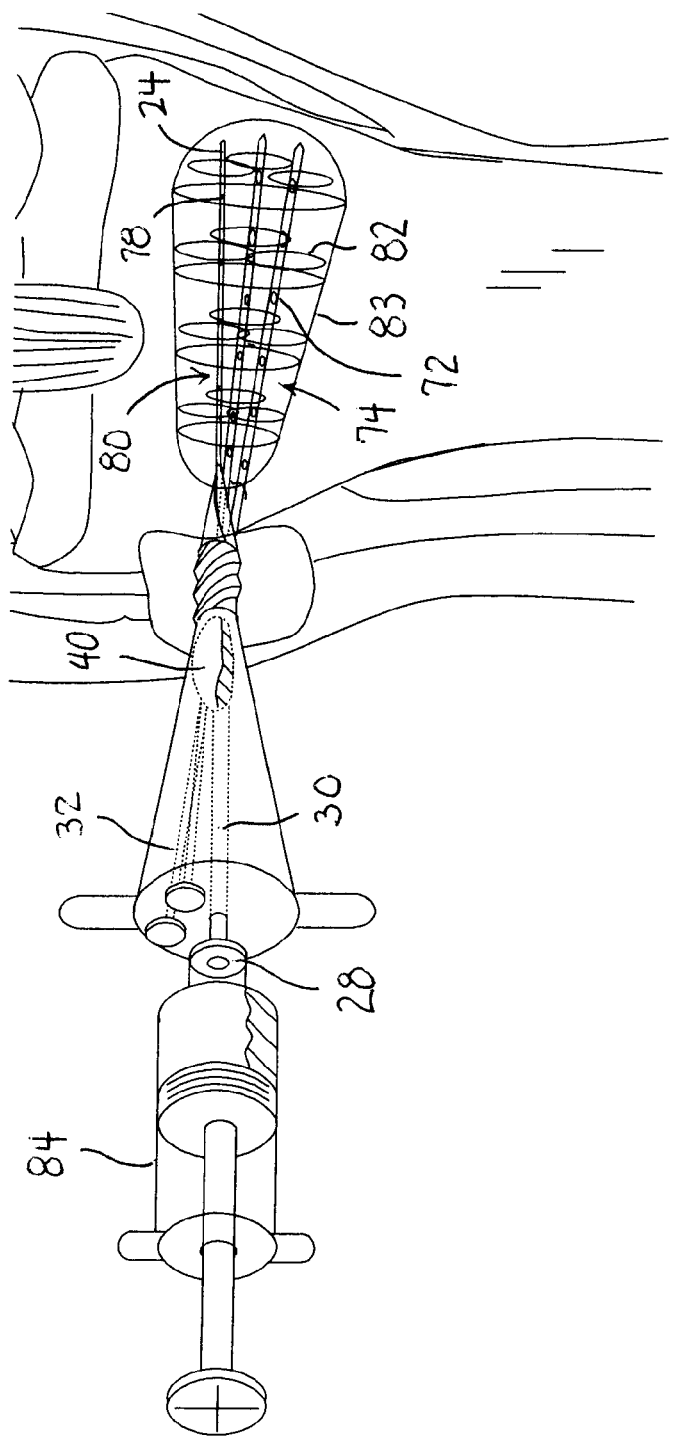
FIG. 14 is the side perspective of the aspiration apparatus of FIG. 1 using the syringe to aspirate an area of harvest.

As shown in FIG. 14, in order to facilitate the drawing of marrow in this preferred embodiment, port 28 and the second portion of lumen 30 are approximately aligned with the wall of chamber 40 to assist the drawing of marrow from chamber 40 into lumen 30 and syringe 84. Similarly, the configuration of chamber 40 can facilitate the downward travel of marrow into the second portion of lumen 30 from needles 14 and/or 24. The position and alignment of port 28 and second lumen 30 as well as the size and shape of chamber 40 is a function of a particular application of aspiration apparatus 10.

The area of harvest 82 for aspiration apparatus 10 preferably has a distally increasing approximately conical shape. This overall conical shape of area of harvest 82 is due to the arrangement, alignment and distally increasing areas of apertures 72 and 78 in needles 14 and 24 that produce distally increasing approximately conically shaped volume of harvest 82 for each needle 14 and 24. The shape of the volume of harvest 82 are a result of the controlled application of Poiseuille's Law to minimize the rate of drawing of marrow from the proximal portions of longitudinal sections 74 and 80 and increase the rate of drawing of marrow in the distal portions of longitudinal sections 74 and 80. It is understood, however, the three dimensional shape of an area of harvest 82 can be advantageously varied depending upon the intended application of aspiration apparatus 10.

When desired, aspiration apparatus is withdrawn from the patient by preferably terminating the application of the external source of pressure and withdrawing needles 14 from the second position to the first position. Guide 12 is removed from the initial incision. The external source of reduced pressure is disconnected from aspiration apparatus 10.

In the preceding specification, the present disclosure has been described with reference to specific exemplary embodiments thereof. It will be evident, however, that various modifications, combinations and changes may be made thereto without departing from the broader spirit and scope of the invention as set forth in the claims that follow. For example, it is understood that the angle of axes-Y relative to axis-X for lumens 32 can vary depending upon the intended application of aspiration apparatus 10 (See FIG. 6). Similarly lumens 32 and needles 14 can be arcuate and define a single rim in chamber 40. In addition, though the present invention is described in terms of a series of embodiments, each embodiment of the present invention can combine one or more novel features of the other embodiments. The specification and drawings are accordingly to be regarded in an illustrative manner rather than a restrictive sense.

What is claimed is:

1. A needle for aspiration that comprises:
    an elongate tubular needle that includes a distal end portion and a proximal end portion, the distal end portion and proximal end portion define a longitudinal axis, the needle has a tubular sidewall and the distal end portion includes a solid distal tip;
    a lumen aligned with the longitudinal axis, the lumen defined by the sidewall and includes a distal terminal end in proximity to the distal tip and an opposed proximal aperture, the proximal aperture adapted to be coupled with an external source of reduced pressure;
    a plurality of apertures defined in the sidewall, each aperture of the plurality of apertures has a defined area in the sidewall that is in fluid communication with the lumen;
    an arrangement of the plurality of apertures, each aperture of the plurality of apertures has a defined location in the sidewall and an angular orientation that defines the angular orientation of a harvest volume for each aperture, the arrangement includes varying the spacing between the locations of the apertures, the spacing between the location of each aperture of the plurality of apertures selectively expanded and reduced to adjust the flow rate of a portion of the plurality of apertures in defined directions, the angle of each aperture varying relative to other apertures to minimize the overlap of flow between apertures, the arrangement and the spacing between the locations of the apertures of the plurality of apertures arranged to minimize harvest volume overlap between the apertures.

2. The needle for aspiration of claim 1, wherein the arrangement of the plurality of apertures further includes varying the size of each aperture of the plurality of apertures to selectively expand and reduce the flow rate of individual apertures in defined directions.

3. The needle for aspiration of claim 1, wherein the needle is arcuate.

4. The needle for aspiration of claim 1, wherein the tip is suitable for penetrating soft tissue.

5. The needle for aspiration of claim 1, wherein the needle includes a window that provides visibility into the lumen.

6. The needle for aspiration of claim 1, wherein the needle includes an alignment device for the angular directional orientation of the needle.

7. A needle for aspiration that comprises:
    an elongate tubular needle that includes a distal end portion and a proximal end portion, the distal end portion and proximal end portion define a longitudinal axis, the needle has a tubular sidewall and the distal end portion includes a solid distal tip;
    a lumen aligned with the longitudinal axis, the lumen defined by the sidewall and includes a distal terminal end in proximity to the distal tip and an opposed proximal aperture, the proximal aperture adapted to be coupled with an external source of reduced pressure;
    a region of the sidewall that extends between a distal end in proximity to the distal tip and extends proximally for a predetermined distance to a proximal end, the region includes a plurality of apertures, each aperture of the plurality of apertures defines an area in the sidewall that is in fluid communication with the lumen; and
    a harvest volume defined by the plurality of apertures in the region when the external source of reduced pressure is applied to the proximal aperture of the lumen for a predetermined period of time, the harvest volume defined by the arrangement of the plurality of apertures in the region, each aperture of the plurality of apertures has a location in the region and an angular orientation, the angular orientation of each aperture of the plurality of apertures aligned to minimize the overlapping between the harvest volume of each aperture, the spacing between the locations of the apertures and angular orientation of the plurality of apertures varying so as to selectively expand the harvest volumes of the apertures and minimize the overlap of the harvest volume of each aperture, the alignment of each aperture of the plurality of apertures and spacing between each of the plurality of apertures defines a controlled rate of harvesting for a predefined shape of harvest volume upon the application of the reduced pressure, the arrangement of the plurality of apertures and the harvest volume adapted for the aspiration of bone marrow.

8. The needle for aspiration of claim 7, wherein the arrangement of the plurality of apertures further includes varying the size of each aperture of the plurality of apertures to selectively expand and reduce the flow rate of individual apertures in defined directions.

9. The needle for aspiration of claim 7, wherein the needle is arcuate.

10. The needle for aspiration of claim 7, wherein the tip is suitable for penetrating soft tissues and fixing the position of the needle in the bone.

11. The needle for aspiration of claim 7, wherein the needle includes a window that provides visibility into the lumen.

12. The needle for aspiration of claim 7, wherein the needle includes an alignment device for the angular directional orientation of the needle and harvest volume of the plurality of apertures.

13. A method of aspirating using an aspiration needle comprising the steps of:
    providing an aspiration needle, the needle has a distal end portion that includes a solid distal tip and a proximal end portion, the needle has a tubular wall that defines a lumen in the needle, the needle and lumen aligned with a central longitudinal axis, the lumen has a distal terminal end in proximity to the distal end portion and a proximal aperture, a plurality of apertures defined in the tubular wall of the needle and the plurality of apertures in fluid communication with the lumen, the plurality of apertures defining an arrangement of the locations and angular orientations of the apertures in the tubular wall and the spacing between the locations of the apertures and angular orientation of the plurality of apertures varying so as to minimize the overlap and selectively expand the harvest volumes of the apertures;

positioning the needle into an incision into a bone of a patient for the application of harvesting bone marrow from a location in a bone having a predefined shape of bone marrow;

placing the needle in position in the incision and inside the bone of the patient for the harvesting of a volume of bone marrow;

connecting an external source of reduced pressure to the proximal aperture of the lumen, aspirating fluid through the plurality of apertures and into the lumen; and harvesting a volume of marrow from the position of the needle inside the bone at a predefined rate of flow through the plurality of apertures over a defined period of time, the rate of flow for the period of time for the plurality of apertures defining a shape of the harvest volume, the shape of the harvest volume determined by the arrangement of the plurality of apertures that includes the location, spacing between each aperture of the plurality of apertures, alignment of each aperture of the plurality of apertures and a rate of flow through of each aperture of the plurality of apertures, the shape of the harvest volume of each aperture minimizing the overlapping of harvest volume of each aperture.

14. The method of claim 13 wherein the step of providing further includes the angular orientation of each aperture of the plurality of apertures having an alignment that minimizes a harvest volume of each aperture overlapping the harvest volume of another aperture.

15. The method of aspirating of claim 13, wherein the step of providing further includes varying the size of the apertures to define the shape of the harvest volume.

16. The method of aspirating of claim 13, wherein the step of harvesting includes harvesting the volume of marrow from a single fixed position of the needle.

17. The method of aspirating of claim 13, wherein the step of harvesting further includes terminating the aspirating from the patient at the predetermined position in the bone at the end of the defined period of time.

18. The method of aspirating of claim 13, wherein the step of positioning includes aligning the direction of the needle for the application of harvesting of the bone marrow in the bone.

19. The method of aspirating of claim 13, wherein the step of harvesting a volume of marrow includes the shape of the harvest volume of the apertures depending upon the application of the needle in the predefined shape of bone marrow.

* * * * *